(12) United States Patent
Mueller

(10) Patent No.: US 6,257,079 B1
(45) Date of Patent: Jul. 10, 2001

(54) TABLET TESTING APPLIANCE

(75) Inventor: Werner G. Mueller, Frankfurt am Main (DE)

(73) Assignee: Erweka GmbH, Heusenstamm (DE)

( * ) Notice: Subject to any disclaimer, the term of this patent is extended or adjusted under 35 U.S.C. 154(b) by 0 days.

(21) Appl. No.: 09/126,085

(22) Filed: Jul. 30, 1998

(30) Foreign Application Priority Data

Jul. 30, 1997 (DE) .............................. 197 33 436

(51) Int. Cl.$^7$ .......................... G01N 33/15; G01G 17/00; G01G 19/00
(52) U.S. Cl. ................................ 73/866; 73/865.8; 177/50
(58) Field of Search .................. 177/50; 73/866, 73/851, 821, 834, 810, 845, 848, 865.8, 865

(56) References Cited

U.S. PATENT DOCUMENTS

| | | | |
|---|---|---|---|
| 4,409,843 | * 10/1983 | Urban et al. | 73/851 |
| 4,472,960 | 9/1984 | Motoyama et al. | 73/7 |
| 4,641,534 | * 2/1987 | Schneider et al. | 73/821 X |
| 4,884,463 | 12/1989 | Kay | 73/865.8 |
| 5,076,107 | * 12/1991 | Timmermans et al. | 73/866 |
| 5,439,036 | 8/1995 | Kraemer | 141/4 |
| 5,515,740 | * 5/1996 | Gamberini | 73/865.8 |
| 5,596,865 | 1/1997 | Kraemer | 53/428 |
| 5,971,038 | * 10/1999 | Fiedler et al. | 73/866 |

FOREIGN PATENT DOCUMENTS

| | | |
|---|---|---|
| GM 8402581 | 6/1984 | (DE) . |
| 4118878 | 1/1993 | (DE) . |
| 4241985 | 6/1994 | (DE) . |
| 685 714 | 12/1995 | (EP) . |
| 2142655 | 2/1973 | (FR) . |
| 7-206144 | * 8/1995 | (JP) . |
| WO 90/01010 | 2/1990 | (WO) . |

OTHER PUBLICATIONS

Patent Abstracts of Japan, abstract of Katsuhiko, JP 07–206144. Aug. 1995.

Derwent abstract of Nippon Alumi KK, JP 08–281220. Oct. 1996.

* cited by examiner

*Primary Examiner*—Thomas P. Noland
(74) *Attorney, Agent, or Firm*—Martin Fleit

(57) ABSTRACT

An appliance for testing oblong tablets or tablests with a similar form and more especially for weighing, measuring and fracture testing of such tablets in suitable testing stations, the appliance including a feeder for feeding individual oblong tablets to a weighing device having a weighing pan with a floor in the form of a trough inclined in the conveying direction, and being provided with a conveyor underneath the weighing pan on which conveyor the tablets are deposited with their longitudinal axis parallel to the longitudinal direction of the trough and which conveys the tablets with such alignment through the further testing stations, and in which between the point at which the oblong tablets are transferred to the conveyor and the testing stations, a toppling device is arranged, which topples over any oblong tablets standing on their edges so that the tablets fall onto their round sides.

19 Claims, 2 Drawing Sheets

TABLET TESTING APPLIANCE

BACKGROUND OF THE INVENTION

The invention relates to an appliance for testing oblong tablets or similarly shaped tablets and more especially for the weighing, measuring and fracture testing of such tablets, in suitable testing stations.

The German utility model 8,402,581 discloses a tablet testing appliance with a conveying means, in the case of which the tablets are passed from a feed means onto a conveying means with a rake, which possesses a plurality of forks which move the tablets further on along a conveying path. A moving means for the rake moves the rake along a distance in the direction of the conveying means, then lifts the rake and moves the rake in the raised state a corresponding distance back again against the conveying direction. After this the rake is lowered and again moved through a certain conveying distance. Along the path of movement of the rake a plurality of testing stations are provided, namely a weighing means, a testing station for measuring thickness and testing station for the fracture test. The known tablet testing appliance is suitable for round or spherical tablets, but less so for so-called oblong tablets and similarly formed tablets, which may possess a substantially oval form in plan view, a flat edge about their periphery and vaulted top and bottoms sides. Such tablets give rise to difficulties with the known appliance. In the various testing stations such as the thickness measuring station, the diameter measuring station and the station for fracture testing they cannot always be aligned in the necessary fashion.

SUMMARY OF THE INVENTION

In contradistinction to this, the invention has the aim of providing for testing of oblong tablets or similarly formed tablets in suitable testing stations, using which a plurality of tests as for example weighing, measuring and fracture testing may be performed in corresponding testing stations, the individual oblong tablets or similarly shaped tablets being able to be positioned in the testing stations with the necessary accuracy.

In order to attain such aims the tablet testing appliance in accordance with the invention is characterized by a feed means for the feed of individual tablets to a weighing means, whose weighing pan possesses a floor, inclined in the direction of conveying, in the form of a trough, and by a conveying means underneath the weighing pan, on which the tablets are deposited from the weighing pan with their longitudinal axis parallel to the longitudinal direction of the trough and which conveys the tablets with such alignment through further testing stations.

Due to this design of the tablet testing appliance of the invention, it is possible to ensure that comparable results are obtained on testing the tablets in the individual testing stations. The thickness of the oblong tablets or similar tablets is defined as the thickness of the tablets perpendicularly to their longitudinal axis and in the middle of the same. Consequently the thickness is measured by placing the tablet on one of its vaulted surfaces and moving a feeler against he opposite vaulted surface in order to measure the distance between the feeler and the engaged surface. Consequently it is necessary for the tablet to be suitably positioned in order to implement such measurement of thickness. The length of an oblong tablet or of a similarly shaped tablet and fracture hardness are measured and, respectively, tested along the longitudinal axis so that a predetermined alignment is necessary in the respective testing station on the longitudinal axis. These requirements can be readily fulfilled with the apparatus of the invention, because the oblong tablets or similar tablets will have the correct alignment when they arrive on the conveying means.

An advantageous embodiment of the tablet testing appliance of the invention is characterized in that the feed means possesses a feed trough inclined in the conveying direction, into which the tablets are fed, more particularly by a vibratory individualizing device. In the feed trough a certain pre-alignment of the tablets may take place.

An advantageous further embodiment of the tablet testing appliance of the invention is characterized in that between the weighing means and the conveying means a flat or shaped transfer trough is provided so that there is the advantage that the alignment of the tablets produced in the weighing means is maintained.

An advantageous further embodiment of the tablet testing appliance of the invention is characterized in that the floor of the weighing pan has a V-shaped cross section. This design of the trough ensures that the tablets are aligned with their longitudinal axis in the V-shaped trough cross section of the floor of the weighing pan, thereby ensuring an optimum alignment of the oblong tablets.

An advantageous further embodiment of the tablet testing appliance of the invention is characterized in that the feed trough and/or the transfer trough also possesses a V-shaped cross section like the trough in the weighing pan.

An advantageous further embodiment of the tablet testing appliance of the invention is characterized in that between the point, at which the oblong tablets coming from the weighing pan are transferred to the conveying means, and the further testing stations, a toppling means, more particularly a wedge, is arranged in the conveying direction, which topples over any oblong tablets standing on their edges so that the tablets fall onto their round side. It is thus possible to ensure that even in this exceptional case the oblong tablets are correctly positioned, before same are fed to the testing stations.

An advantageous further embodiment of the tablet testing appliance of the invention is characterized in that the conveying means possesses a conveying rail and a rake, which moves the tablets forward on the conveying rail. This makes it possible to ensure that the alignment of the oblong tablets, as the tablets come from the weighing means, is maintained during further conveying.

Lastly, an advantageous further embodiment of the tablet testing appliance of the invention is characterized in that the toppling means can have the form of a toppling stone in the conveying direction, more particularly a wedge, a toppling groove in the conveying direction, or preferably an individually and vertically movable toppling element that can be moved to extend over the conveying plane to form a toppling stone, and that can be withdrawn under the conveying plane to form a toppling groove. Of course, the toppling element can take intermediate poisons, for example flush with the conveying plane, in case the probe does not need to be toppled. Thus, the height or depth of the toppling element can individually be varied within the limits of it's maximum movement, according to the form of the probe.

BRIEF DESCRIPTION OF THE DRAWINGS

One working embodiment of the invention will be now described with reference to the accompanying drawings.

DETAILED DESCRIPTION OF PREFERRED EMBODIMENTS

Figure 1:
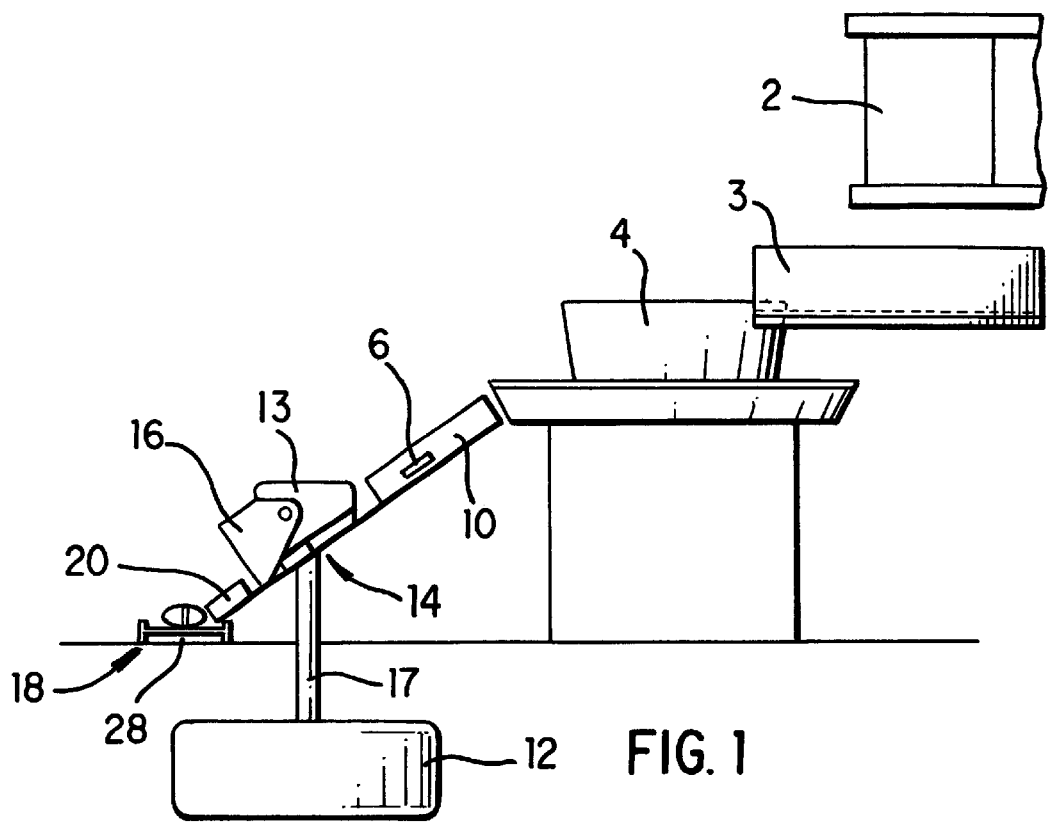
FIG. 1 shows a diagrammatic side elevation of the top part of a tablet testing appliance.
Figure 2:
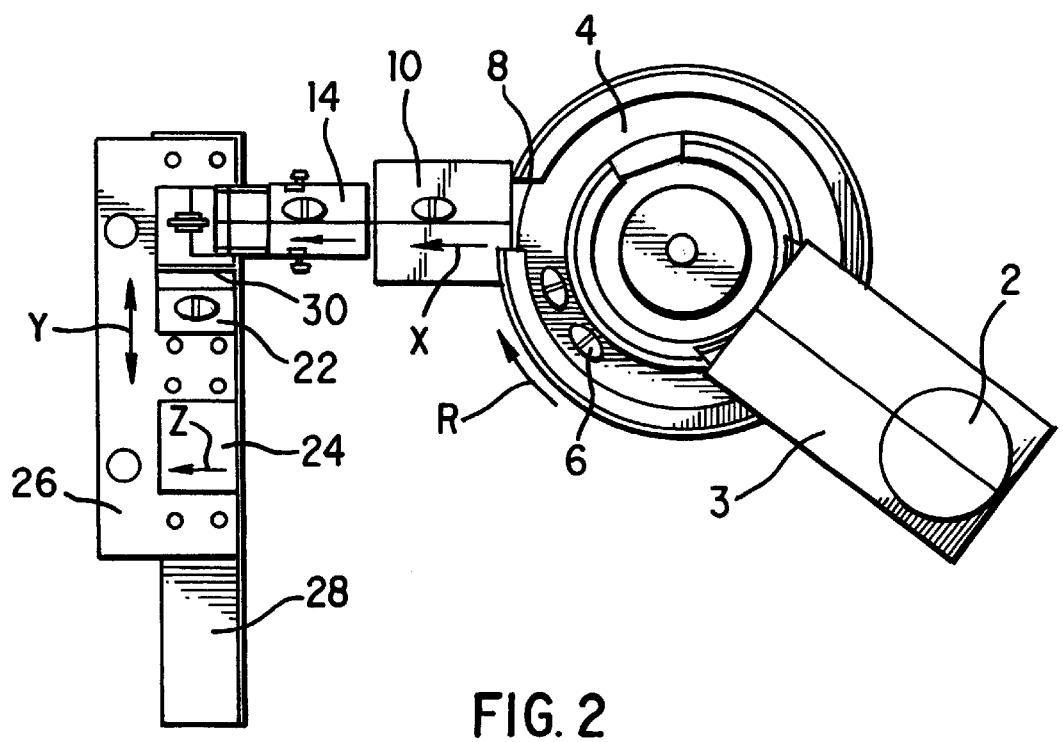
FIG. 2 shows a partial plan view of the tablet testing appliance in accordance with FIG. 1.

As will be seen from FIGS. 1 and 2, the tablet testing appliance comprises a magazine 2 or, respectively, a storage container for tablets. The oblong tablets move from the magazine 2 to a vibratory individualizing means, which comprises a longitudinal conveying trough 3 and a carousel conveyor 4. Both the longitudinal conveying trough 3 and also the carousel conveyor 4 may be omitted in certain possible forms of the appliance. The tablets 6 are moved by the carousel conveyor 4 in the direction of the arrow R (FIG. 2) and discharged through a dispensing opening 8 into a feed trough 10, which belongs to the feed means and is inclined in the conveying direction (arrow X, FIG. 2) from the outlet opening 8 of the carrousel conveyor 4 downward. From the feed trough 10 the tablets are transferred to a weighing means 12, whose weighing pan 13 possesses a floor 14 in the form of a trough or groove inclined in the direction of conveying. The weighing pan 13 is closed at its bottom end by a flap 16, which may be moved out of the way of the tablets so that the tablets may leave the weighing pan 13. The weighing pan 13 with the bottom 14 and the flap 16 is connected with the weighing means 12 by means of a connecting line 17.

Between the weighing means 12 and a conveying means for the oblong tablets, a transfer trough 20 is provided.

The weighing pan 13 has a V-shaped cross section in its bottom 14. The feed trough 10 and/or the transfer trough 20 may have a corresponding V-shaped cross section or a flat configuration.

The conveying means 18 is provided underneath the weighing pan 13 and underneath the transfer trough 20, and the oblong tablets are deposited from the weighing pan 16 on the floor 14 of the weighing pan with their longitudinal axis parallel to the longitudinal direction of the trough. The conveying means, which comprises a conveying rail 28 and a rake 26, conveys the tablets with this alignment through further testing stations, more particularly a testing station 22 for thickness measurement, in which a thickness measuring sensor is moved from above onto the tablets, and a testing station 24, in which the diameter and the fracture hardness of the tablets are measured. The double arrow Y indicates that the rake 26 is a reciprocated over the conveying rail 28 (FIG. 1) in order to convey the oblong tablets through the testing station. On that part of the testing station 24 where the fracture hardness test is performed, a crushing jaw (not illustrated) acts in the direction of the arrow Z on the oblong tablets in the longitudinal direction thereof.

Between the point at which the oblong tablets coming from the weighing pan 13 are transferred to the conveying means 18, and the further testing stations 22 and 24, a toppling means or a wedge 30 is arranged in the conveying direction, which pushes over any oblong tablets standing on their peripheral edge, so that the tablets topple onto their round side.

Figure 3A:
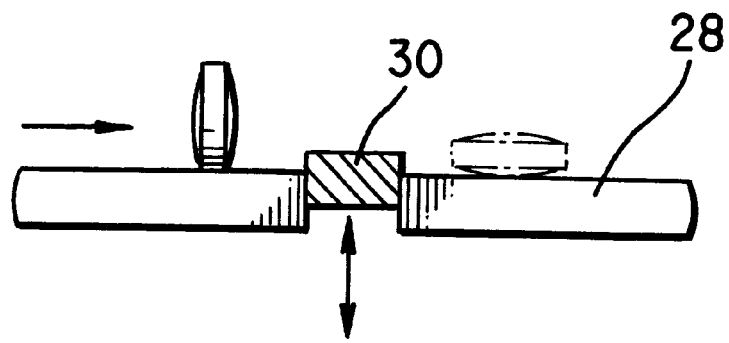
FIGS. 3a–c show a side view of a detail of the tablet testing appliance in accordance with FIG. 1.
Figure 3B:
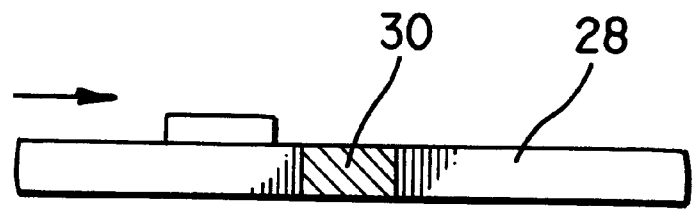
Figure 3C:
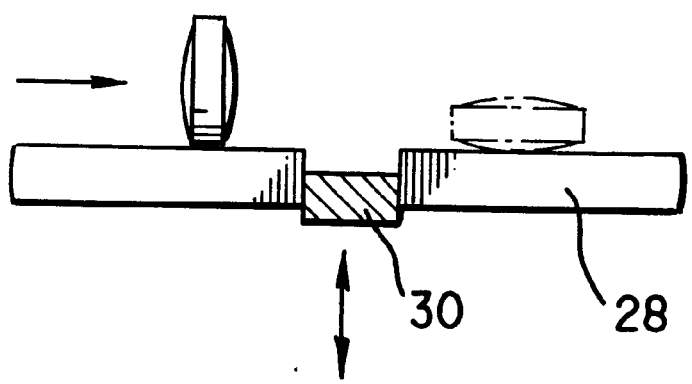

FIG. 3 shows an embodiment of a tablet testing appliance in accordance with FIG. 1, in which the toppling means are constructed as a vertically movable toppling element 30 oriented perpendicularly to the conveying direction that can be moved to extend over the conveying plane to form a toppling stone, and that can be withdrawn under the conveying plane to form a toppling groove. FIG. 3a shows the toppling element 30 in a position extending over the conveying plane to form a toppling stone; FIG. 3b shows the toppling element 30 in a position flush with the conveying means 28, and FIG. 3c shows the toppling element 30 in a position withdrawn under the conveying plane to form a toppling groove.

It will be apparent from the preceding description that the oblong tablets or similar tablets are positioned with the correct alignment in the testing stations 22 and 24 where accurate alignment of the oblong tablets is paramount.

It is to be understood that the above description is intended to be illustrative and not restrictive. Many embodiments will be apparent to those skilled in the art upon reviewing the above description. The scope of the invention should, therefore, not be limited to the specific embodiments described above, but should instead be determined with reference to the appended claims along with the full scope of equivalence to which such claims are entitled.

What is claimed is:

1. An appliance for testing oblong tablets by weighing, measuring and fracture testing of such tablets, in at least one testing station, comprising:
    a feed means for feeding individual tablets to a weighing means comprising a weighing pan having a floor, inclined in the direction of the conveying, in the form of a trough, and
    a conveying means underneath the weighing pan, on which the tablets are deposited from the weighing pan with their longitudinal axis parallel to the longitudinal direction of the trough and which conveys the tablets with such alignment through further testing stations.

2. The tablet testing appliance as claimed in claim 1, wherein the floor of the weighing pan has a V-shaped cross section.

3. The tablet testing appliance as claimed in claim 1, wherein the feed means comprises a feed trough inclined in relation to the conveying means, into which feed trough the tablets are fed.

4. The tablet testing appliance as claimed in claim 3, wherein the tablets are fed into the feed trough by a vibratory individualizing means.

5. The tablet testing appliance as claimed in claim 3, wherein the feed trough has a V-shaped cross section.

6. The tablet testing appliance as claimed in claim 1, wherein a transfer trough is arranged between the weighing means and the conveying means.

7. The tablet testing appliance as claimed in claim 6, wherein the transfer trough has a V-shaped cross section.

8. The tablet testing appliance as claimed in claim 1, wherein between the point at which the oblong tablets coming from the weighing pan are transferred to the conveying means, and the further testing stations, a toppling means is arranged in the conveying direction, which topples over any oblong tablets standing on an edge thereof so that such tablets fall onto a round side thereof.

9. The tablet testing appliance as claimed in claim 8, wherein the toppling means comprise a wedge which is arranged in the conveying direction and topples over any oblong tablets standing on its edge.

10. The tablet testing appliance as claimed in claim 1, wherein the conveying means comprises a conveying rail and a rake, which moves the tablets forward on the conveying rail.

11. An appliance for testing oblong tablets by weighing, measuring and fracture testing of such tablets, in at least one testing station, said apparatus comprising a conveying means, for conveying tablets deposited thereon through the testing stations wherein a toppling means is arranged between the point at which the oblong tablets are transferred to the conveying means and the testing stations, which topples over any oblong tablets standing on an edge thereof so that the tablets fall onto a round side thereof and wherein the toppling means comprise a vertically movable toppling stone oriented perpendicularly to the conveying direction.

12. The tablet testing appliance as claimed in claim 11, wherein the toppling stone can be withdrawn under the conveying plane to form a toppling groove.

13. The tablet testing appliance as claimed in claim 11, wherein the toppling means comprise a vertically movable toppling element oriented perpendicularly to the conveying direction that can be moved to extend above the conveying plane to form a toppling stone, and that can be withdrawn under the conveying plane to form a toppling groove.

14. An appliance for testing oblong tablets by weighing, measuring and fracture testing of such tablets, in at least one testing station, said apparatus comprising a conveying means, for conveying tablets deposited thereon through the testing stations wherein a toppling means is arranged between the point at which the oblong tablets are transferred to the conveying means and the testing stations, which topples over any oblong tablets standing on an edge thereof so that the tablets fall onto a round side thereof and wherein a feed means for feeding individual tablets to a weighing means which comprises a weighing pan having a floor in the form of a trough inclined in the direction of conveying is disposed above the conveying means, and the tablets are deposited from the weighing pan onto the conveying means with their longitudinal axis aligned parallel to the longitudinal direction of the through, said tablet testing appliance conveying the tablets with such alignment through further testing stations.

15. The tablet testing appliance as claimed in claim 14, wherein the feed means comprises a feed trough inclined in relation to the conveying means, into which feed trough the tablets are fed by a vibratory individualizing means.

16. The tablet testing appliance as claimed in claim 15, wherein a transfer trough is arranged between the weighing means and the conveying means.

17. The tablet testing appliance as claimed in claim 16, wherein the floor of the weighing pan has a V-shaped cross section.

18. The tablet testing appliance as claimed in claim 17, wherein at least one of the feed trough and the transfer trough has a V-shaped cross section like the floor of the weighing pan.

19. The tablet testing appliance as claimed in claim 14, wherein the conveying means comprises a conveying rail and a rake which moves the tablets forward on the conveying rail.

* * * * *